(12) United States Patent
Brieske (10) Patent No.: US 7,367,540 B2
(45) Date of Patent: May 6, 2008

(54) FAST CLOSING CLAMP

(75) Inventor: Gerhard Brieske, Ampfing (DE)

(73) Assignee: Lifebridge Medizintechnik AG, Ampfing (DE)

( * ) Notice: Subject to any disclaimer, the term of this patent is extended or adjusted under 35 U.S.C. 154(b) by 76 days.

(21) Appl. No.: 11/366,914

(22) Filed: Mar. 2, 2006

(65) Prior Publication Data
US 2006/0197040 A1 Sep. 7, 2006

(30) Foreign Application Priority Data
Mar. 4, 2005 (EP) .................................. 05004835

(51) Int. Cl.
*F16K 35/00* (2006.01)
(52) U.S. Cl. .................. 251/75; 251/4; 251/7; 251/71
(58) Field of Classification Search ............ 251/4, 251/7, 70, 71, 75
See application file for complete search history.

(56) References Cited
U.S. PATENT DOCUMENTS

| | | | |
|---|---|---|---|
| 3,463,443 A | * | 8/1969 | Churchill .................. 251/70 |
| 3,512,421 A | * | 5/1970 | Anderson .................. 74/89.25 |
| 4,105,028 A | | 8/1978 | Sadlier et al. |
| 4,596,374 A | | 6/1986 | Thompson et al. |
| 5,445,613 A | | 8/1995 | Orth |
| 6,386,505 B2 | * | 5/2002 | Schob ..................... 251/7 |

FOREIGN PATENT DOCUMENTS

| | | |
|---|---|---|
| DE | 39 18 449 A1 | 12/1990 |
| DE | 199 00 320 C1 | 7/2000 |
| EP | 0 241 123 A1 | 10/1987 |
| EP | 0 718 001 A2 | 6/1996 |
| EP | 1 086 712 A2 | 3/2001 |
| EP | 1 132 108 A1 | 9/2001 |

* cited by examiner

*Primary Examiner*—John K. Fristoe, Jr.
(74) *Attorney, Agent, or Firm*—Workman Nydegger (57) ABSTRACT

The invention relates to a fast closing clamp for the pinching off of hoses, wherein the fast closing clamp has a clamp jaw with a clamping position, in which it can pinch off a hose, and an open position. The fast closing clamp in accordance with the invention furthermore comprises a holding apparatus, a spring device and a latch device as well as a return mechanism.

19 Claims, 5 Drawing Sheets

FAST CLOSING CLAMP

The invention relates to a fast closing clamp for the pinching off of hoses

Liquids, in particular blood, are transported in medical devices, for example heart-lung machines. A heart-lung machine serves inter alia to take over the function of the heart and of the lung of a patient during a heart operation and to maintain the blood circulation. It is particularly important in this process that no air bubbles are transported so as not to endanger the patent. For this purpose, a bubble detector is provides at a suitable position in the fluid circuit in medical devices of this type. If an air bubble is detected in the extracorporeal blood circuit by this detector, the circuit has to be interrupted immediately so that an endangering of the patient is precluded. Clamping apparatus which engage at a hose of the fluid system serve for this purpose.

The compression of the hose by the clamping apparatus must take place as fast as possible in this process and should only have some milliseconds up to 100 milliseconds of delay.

U.S. 5,445,613 describes a clamping apparatus which is held open against the spring force of a spring either electromagnetically or pneumatically. A switching off of the electromagnet and a disconnection of the air pressure permit a relaxation of the spring which results in a closing of the clamping apparatus. To open the clamping apparatus again, current must again be conducted through the electromagnetic or the pneumatic system must again be charged with air pressure. To keep the clamping apparatus open, current must therefore flow permanently through the electromagnet here or the air pressure in the pneumatic apparatus must be maintained, which is in particular disadvantageous in mobile units due to the high energy requirement.

DE 199 00 320 C1 describes an apparatus in which a clamp jaw is held by a holding element against the force of a spring. The holding element engages into a cut-out of the clamp jaw, with it being held in this position by an electromagnetic apparatus. As long as the electromagnetic apparatus has current applied, the holding element holds the clamp jaw. Switching off the current releases the holding element from the clamp jaw which thereupon moves to its closed position driven by the spring. To open the clamping apparatus again, the clamp jaw is pushed back from the oppositely disposed side with the help of a second apparatus.

EP 1132108 A1 describes an apparatus which generates two equilibrium positions for a clamping device with the help of permanent magnets. One of these equilibrium positions corresponds to the closed position of the clamping apparatus, whereas the other equilibrium position corresponds to the open position. The clamping apparatus is moved to and fro between these two equilibrium positions with the help of an electromagnet.

It is the object of the present invention, to provide a fast closing clamp for portable units whose design is compact and reliable and which requires little energy.

This object is satisfied by a fast closing clamp having the features of claim 1. Preferred embodiments are the subject of the dependent claims.

A fast closing clamp in accordance with the invention for the pinching off of hoses has a clamp jaw with a clamp position in which it can pinch off a hose. The clamp jaw furthermore has an open position. A holding apparatus is provided relative to which the clamp jaw is biased by a spring device so that the clamp jaw is brought into the clamping position on relaxation of the spring. A latch device serves to latch the clamp jaw and the holding apparatus to one another in a latched position against the spring force of the spring device. Finally, the fast closing clamp in accordance with the invention has a return mechanism with whose help the clamp jaw can be moved back from the clamping position into its open position with the holding apparatus. The return mechanism in this process serves for the movement of the holding apparatus relative to the clamp jaw until the holding apparatus and the clamp jaw are in their latched position relative to one another. This movement takes place while the clamp jaw is in the clamping position. The return mechanism furthermore serves to subsequently move the holding mechanism together with the clamp jaw into the open position of the clamp jaw after the clamp jaw and the holding apparatus with the latch device have been latched with one another.

The fast pinching off of the hose can be carried out very precisely and reliably using the fast closing clamp in accordance with the invention. The clamp jaw is latched in the holding apparatus in the open position of the clamp jaw. In this process, it is biased relative to the holding apparatus via the spring force of the spring. If, for example, a bubble detector in a heart-lung machine detects an air bubble in the fluid system, the latch device is released. The clamp jaw is brought out of the holding apparatus into the clamping position by the spring very fast, as a rule within some milliseconds up to 100 milliseconds. In the clamping position, the clamp jaw, for example, presses a hose of the heart-lung machine against a wall, e.g. the rear wall of a passage, in which the hose is guided. The wall thereby forms a passive counter-support for the clamp jaw. A very fast reaction for the closing of the hose is therefore ensured.

The clamping apparatus can be guided back into the open position again in a very simple and substantially mechanical manner using the apparatus in accordance with the invention. A return mechanism which moves the holding apparatus relative to the clamp jaw so far until the clamp jaw and the holding apparatus are in their latched position relative to one another serves for this purpose. While the holding apparatus is moved by the return mechanism, the clamp jaw remains in its clamping position and is still supported against the passive counter support.

After the holding apparatus has been moved so far that the holding apparatus and the clamp jaw are in their latched position relative to one another, the latch device is activated so that the clamp jaw and the holding apparatus are latched to one another. The holding apparatus is then moved together with the clamp jaw with the help of the return mechanism so that the clamp jaw moves into its open position. The fast closing clamp in accordance with the invention can therefore be moved back into the open position in a very simple and mechanical manner. The system is robust and less prone to problems.

The spring device is tensioned again even while the return mechanism moves the holding apparatus relative to the clamp jaw. During the moving back of the holding apparatus together with the clamp jaw, the release energy is therefore already fully available again so that, optionally, the clamp jaw can already be released again and the hose pinched off again during the moving back. There is thus no period during which a closing of the hose is not possible.

The clamp jaw and the holding apparatus can be displaceably supported with respect to one another in a different manner. A secure and simple embodiment has a hollow part in which the clamp jaw is guided as the holding apparatus.

The spring device is connected to the holding device and to the clamp jaw such that the clamp jaw and the holding device move apart on the relaxation of the spring. In an embodiment with a hollow part as the holding device, this can be done simply and in a manner easy to establish with the help of seats. A first seat is provided inside the hollow part and a second seat at the outside of the clamp jaw. The spring device is tensioned between these seats.

The latching of the holding apparatus and of the clamp jaw to one another advantageously takes place mechanically so as to have to operate as few energy-consuming elements as possible.

A simple embodiment provides for this purpose at least one element which engages laterally from the clamp jaw into a corresponding cut-out of the holding apparatus in the latched state and frees the cut-out in an unlatched state. It can, for example, be a question of bars or balls which are pressed out of the clamp jaw mechanically to engage into the cut-out of the holding apparatus. An advantageous embodiment comprises one or more balls which project laterally out of the clamp jaw through openings which partly enclose the balls in the latched state. In the unlatched state, the balls do not project beyond the lateral extent of the clamp jaw and thus do not latch the clamp jaw in the holding apparatus.

Particularly with a mechanical latch device, a blocking bar can be provided for the actuation of the latch device. The blocking bar can, for example, be moved with the help of an electrical drive to unlatch the latch device. The drive must then only be operated for a short time until the unlatching has taken place. An electromagnet can e.g. be used as the drive.

A preferred embodiment of the fast closing clamp in accordance with the invention comprises a spindle drive for the return mechanism which is driven, for example, by an electric motor to move the holding apparatus together with the clamp jaw back out of the clamping position.

A particularly secure embodiment comprises a mechanism which bounds the movement of the clamp jaw triggered by the spring device, that is, for example, prevents the clamp jaw from being able to move completely out of a housing. A corresponding abutment apparatus is e.g. provided for this purpose. This significantly increases security particularly with portable systems. An unintentional triggering of the fast closing clamp, e.g. during transport, cannot have the result that the clamp jaw is fully driven out of the housing by the effect of the spring device.

To secure the fast closing clamp in the non-used state or to prevent the fast closing clamp from being triggered even though a pinching off is not even desired, a fixing device can be provided for the fixing of the clamp jaw and of the holding apparatus. The holding apparatus and the clamp jaw can, for example, be fixed in a housing with the help of the fixing device for this purpose.

The fast closing clamp in accordance with the invention can be used wherever the pinching off of a hose is required. The fast closing clamp in accordance with the invention is particularly suitable for medical devices since a faster, more secure, and more precise termination of a hose connection is required in many cases there.

The fast closing clamp of the invention is compact and simple in design. It is therefore in particular suitable for portable systems.

The invention will be explained in detail with reference to an embodiment which is shown in the enclosed Figures. There are shown.

Figure 1:
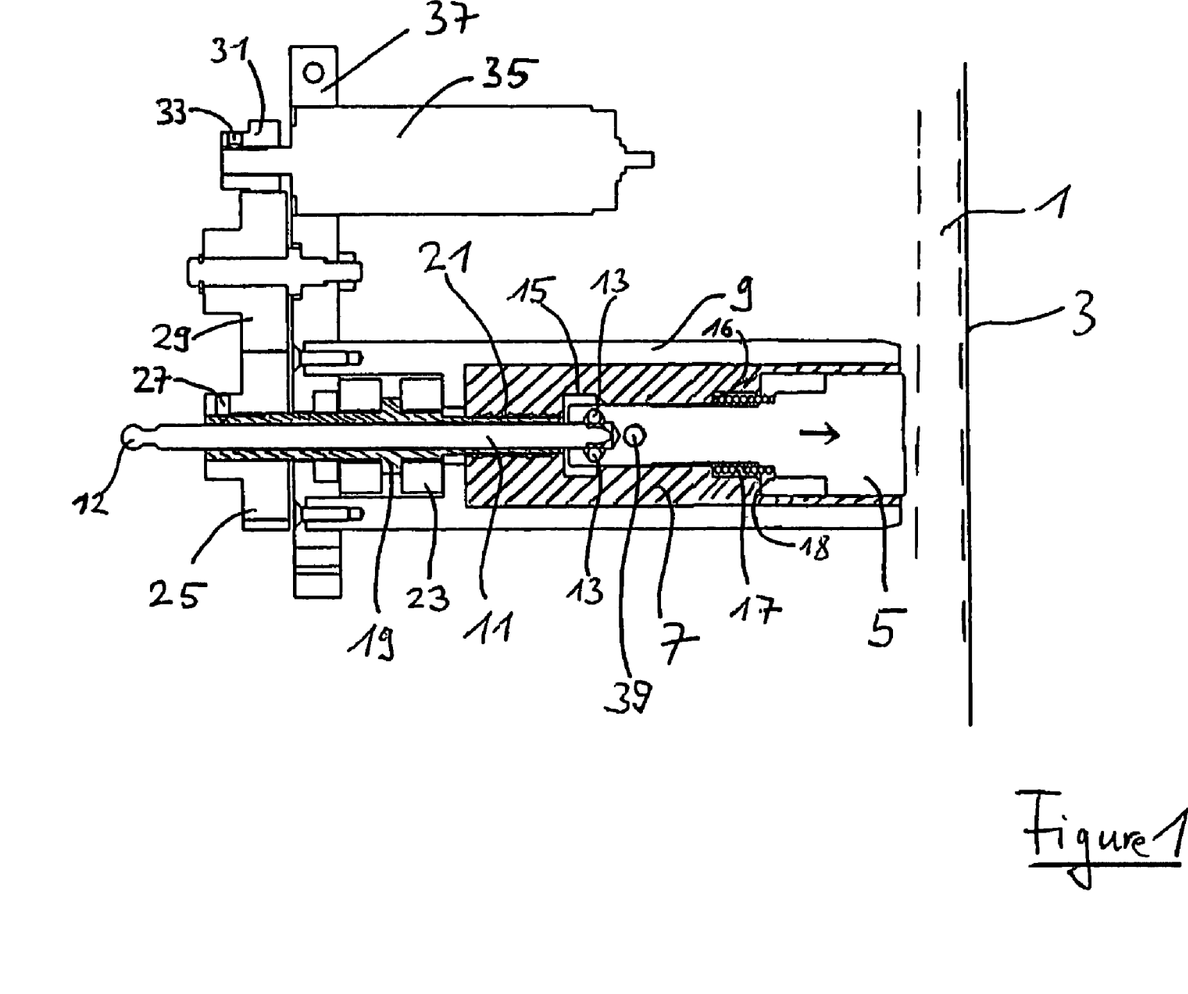
FIG. 1 a lateral section through a fast closing clamp in accordance with the invention.
Figure 3:
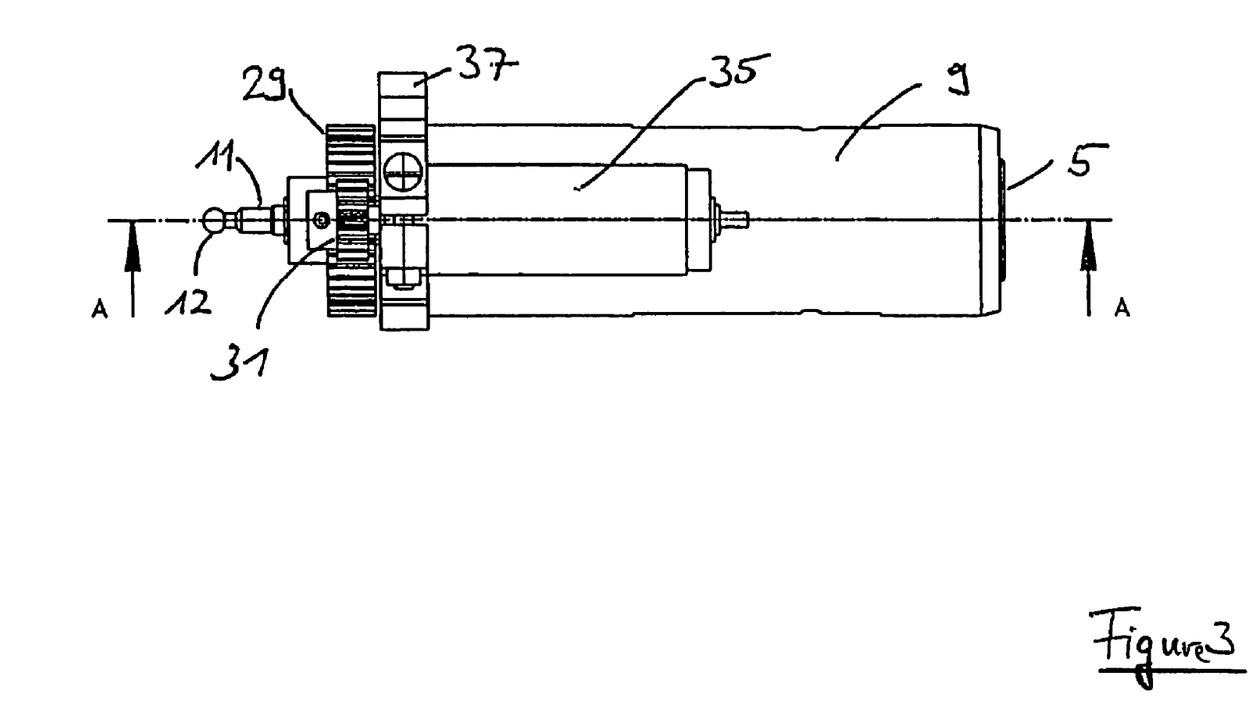
FIG. 3 a plan view in the direction III indicated in FIG. 2.

The sectional view of FIG. 1 corresponds to the cross-section indicated by A in FIG. 3. 1 designates a hose which should optionally be pinched off, e.g. inside a heart-lung machine. As soon as e.g. an air bubble is detected in this hose in the blood flowing therein by a detector (not shown), the hose clamp must pinch off the hose. The hose contacts a wall 3 which is e.g. formed by the rear wall of a housing part receiving the hose. A clamp jaw 5, which has to be brought into a clamping position in the arrow direction by the fast closing clamp, serves to pinch off the hose 1.

Reference numeral 7 designates a holding apparatus which has an inner hollow space in which the clamp jaw 5 is guided. In the embodiment shown, the clamp jaw 5 is made as an internal piston and the holding apparatus 7 as an external piston, with the internal piston 5 being displaceably received in the external piston 7 and the external piston 7 being displaceably received in a housing 9. A spring 17 is supported against a seat 16 inside the external piston 7 and a seat 18 is supported at the external periphery of the internal piston 5, said spring being under compressive tension in the open position of the internal piston shown in FIG. 1.

19 designates the spindle of a spindle drive which has an external thread 21 in the region in which it engages into the external piston 7. The external piston 7 has a corresponding mating thread at the internal periphery where the spindle 19 passes through it. The spindle 19 is rotatably held in the housing 9 in a bearing 23. To drive the spindle, it is connected to a toothed wheel 25 via the grub screw 27. The toothed wheel 25 meshes with a toothed wheel 29 which in turn meshes with a toothed wheel 31. The toothed wheel 31 is connected via a grub screw 33 to the axis of an electric motor 35 which is fixedly installed in a holding plate 37.

The toothed wheel 29 is rotatably supported in the holding plate 37. The housing 9 is finally fixedly connected to the holding plate 37.

A hollow space 15 is located in the external piston 7 and balls 13 can partly enter into it which project radially out of the internal piston 5 in the latched state. This detail will be explained with reference to FIG. 4.

Figure 2:
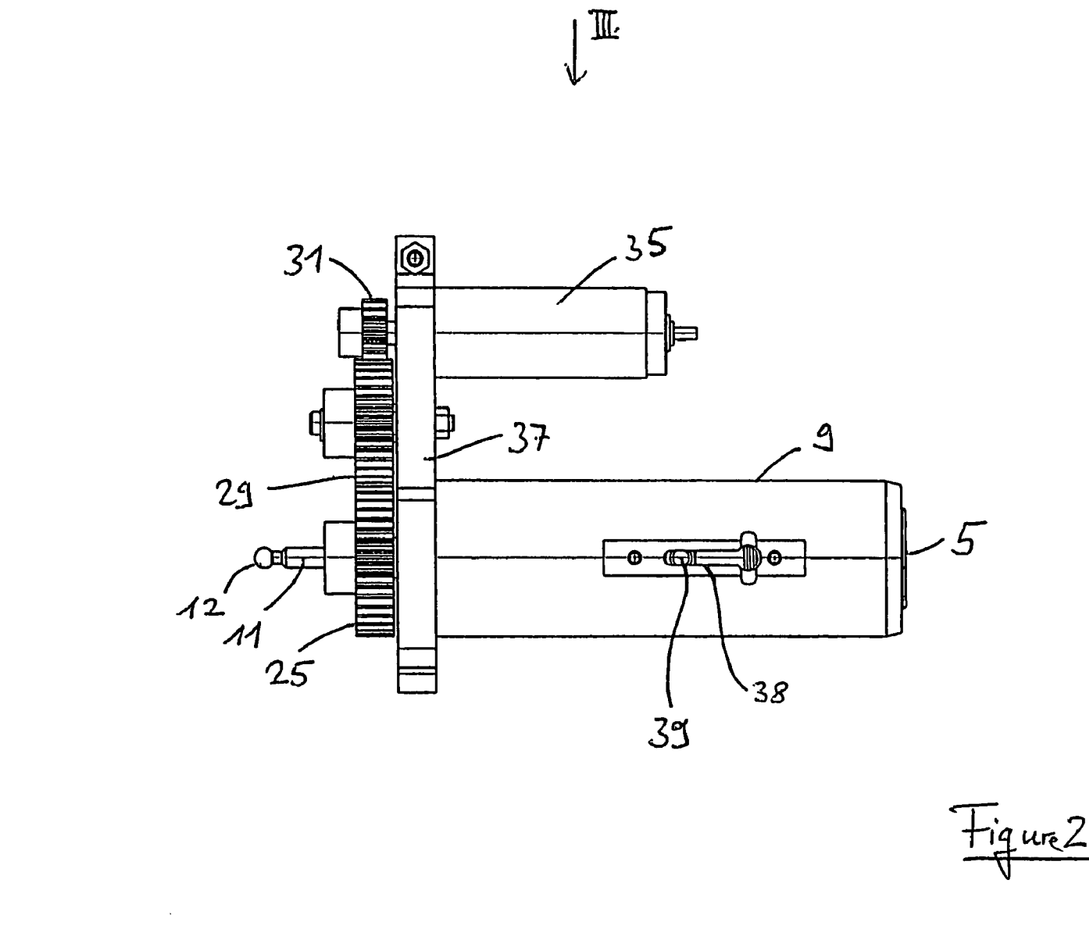
FIG. 2 a lateral plan view of a fast closing clamp in accordance with the invention.

FIG. 2 shows the fast closing clamp of FIG. 1 in a lateral plan view. The direction of view which is visible in the plan view of FIG. 3 is indicated by III in FIG. 2. The internal piston 5 comprises a radially outwardly extending abutment bar 39 which is guided in an elongate hole 38 of the housing 9, as can be recognized in FIG. 2.

Figure 4:
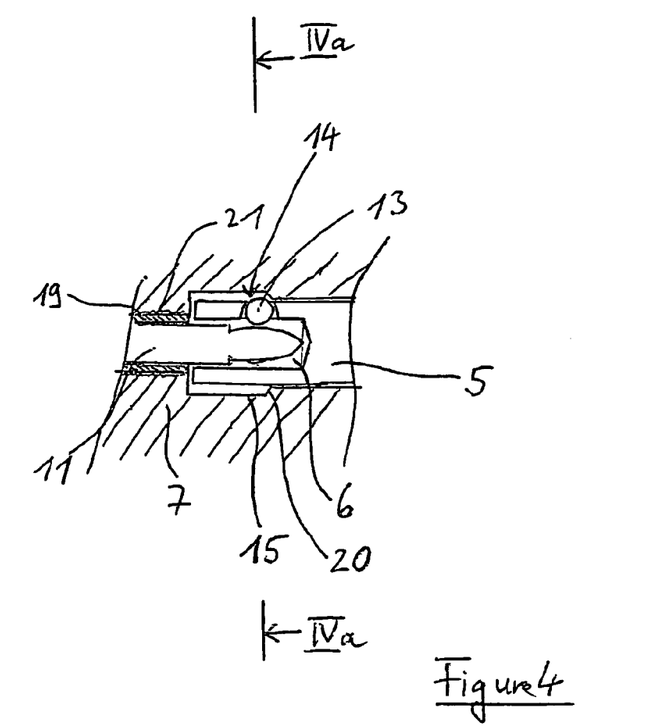
FIG. 4 a detail of the sectional view of FIG. 1.

FIG. 4 shows a detail of FIG. 1 in the region of the latch device between the external piston 7 and the internal piston 5. The latched state is also shown in FIG. 4. The tip of the blocking bar 11 lies in the axial cut-out 6 of the rear part of the internal piston 5. In this process, the tip presses balls 13 outwardly through radial openings 14 in the internal piston 5 which partly enclose the balls 13. The tip of the blocking bar 11 is made in ball shape and tapered toward the front so that it can easily be pushed between the balls 13. In the embodiment shown, three of the radial openings 14 are provided with corresponding balls 13 at an angle of 120° to one another. The two other openings are therefore not visible in the sectional representation of FIG. 4.

The balls 13 engage into a cut-out 15 in the external piston 7. In the state shown, the internal piston 5 can accordingly not move out of the external piston 7 to the right since the balls 13 are fixed in the cut-out 15 of the external piston 7. If the blocking bar 11 is pulled out of the axial cut-out 6 of the internal piston 5 to the left, the balls can move into the axial cut-out 6 and the internal piston 5 can be moved out of the external piston 7 to the right by the force of the spring 17. The inward movement of the balls 13 is in particular facilitated by the chamfering 20 of the cut-out 15.

Finally, the right hand end of the spindle 19 can be recognized in FIG. 4 with the thread 21 which meshes in an internal thread of the external piston 7.

Figure 4A:
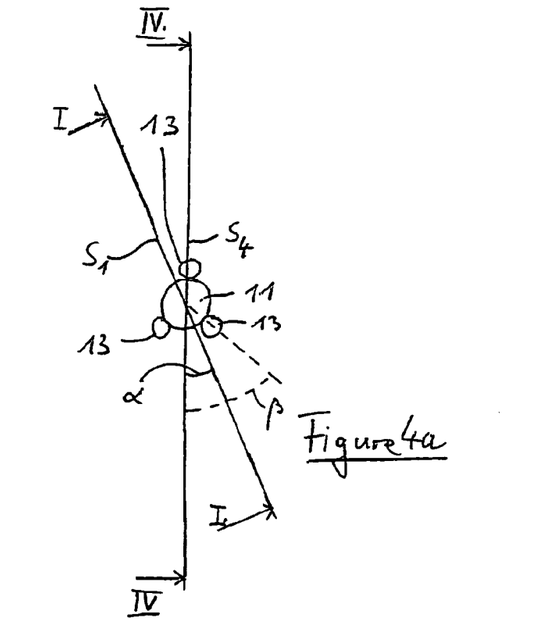
FIG. 4a in a schematic representation, a cross-sectional view in an axial direction of view, designated by IVa in FIG. 4, of the blocking bar of an embodiment in accordance with the invention.

Whereas FIG. 4 shows a section through the fast closing clamp in which a ball 13 is sectioned precisely at the center, FIG. 1 shows a section in which no ball 13 is precisely cut. In this respect, the sectional planes of FIG. 1 and of FIG. 4 are tilted with respect to one another by 30° around an axis which is, for example, defined by the blocking bar 11. This relationship is illustrated in FIG. 4a which shows a view in the direction of the arrows IVa which are given in FIG. 4. A view in an axial direction of the tip of the blocking bar 11 and of the balls 13 is shown in a schematic representation in FIG. 4a. $S_1$ shows the sectional plane of FIG. 1, while $S_4$ shows the sectional plane of FIG. 4. The direction of view of the sectional plane, which is the subject matter of FIG. 1, is designated by the arrows I in FIG. 4a. The direction of view of the sectional plane, which is the subject matter of FIG. 4, is designated by the arrows IV in FIG. 4a. The angle β indicated amounts to 60°, whereas the tilt angle of the sectional plans α amounts to 30°.

Figure 5:
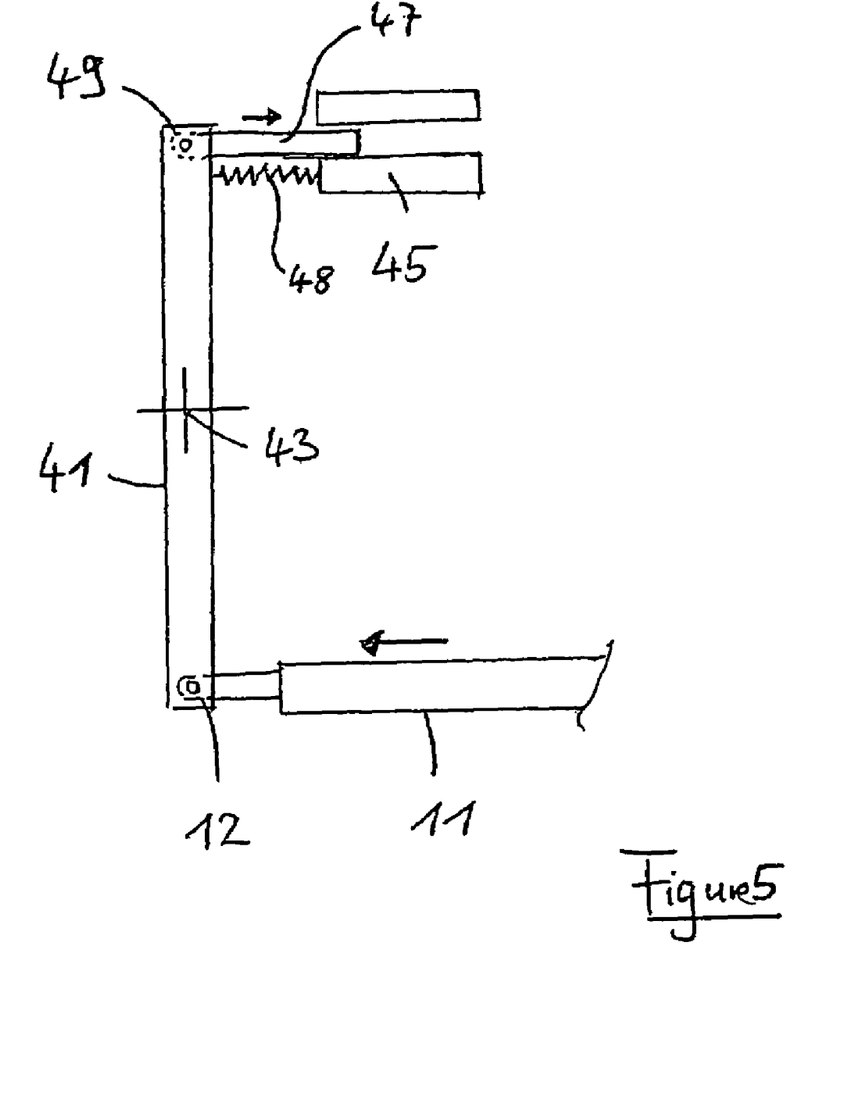
FIG. 5 in a schematic representation, a detail of the fast closing clamp in accordance with the invention which is not shown in FIGS. 1 to 3.

FIG. 5 shows, in a schematic representation, a part of the fast closing clamp which is not shown in FIGS. 1 to 4. It is a mechanism which serves for the movement of the blocking bar 11 in the axial direction. The blocking bar 11 is connected via a hinge point 12 to a rocker 41 which is rotatably supported at the point 43. This rocker is connected via a hinge point 49 to a metallic actuation bar 47 which projects into an electromagnet 45. In this process, the arrangement is selected such that the bar 47 moves to the right on a flow of current through the electromagnet 45. The rocker rotates around the center of rotation 43 and moves the blocking bar 11 to the left in the representation of FIG. 5.

Reference numeral 48 designates a compression spring which biases the rocker 41, the actuation bar 47 and the blocking bar 11 in the direction of their positions of rest when the electromagnet 45 again has no current. The force of the electromagnet 45 acts against the spring force of this spring 48.

A fast closing clamp in accordance with the invention is used as follows. If a bubble is detected in the transported liquid in the hose 1 by the detector (not shown), a signal is transmitted to the electromagnet 45. The electromagnet 45 is put under current for approximately 50 ms so that the actuation bar 47 moves into the electromagnet. The rocker 41 rotates around the center of rotation 43 and pulls the blocking bar 11 to the left in accordance with the representation of the Figures. The blocking rod 11 thereby moves out of the axial hollow space 6 (FIG. 4) of the internal piston 5. The internal piston 5 is urged in the direction of the arrow, which is given in FIG. 1, by the spring force of the spring 17. Since the blocking bar 11 no longer blocks the axial hollow space, the balls 13 —facilitated by the chamfer 20 —escape back into this hollow space 6 and the latch connection between the internal piston 5 and the external piston 7 is cancelled. The spring force of the spring 17 drives the internal piston 5 against the hose 1 and pinches it off against the rear wall 3 of the passage conducting the hose. It is, for example, sufficient to operate the electromagnet only for approximately 50 milliseconds to trigger this action. The hose is pinched off after only around 100 milliseconds.

The abutment bar 39 guided in the longitudinal hole 38 in the housing 9 prevents the internal piston 5 from being able to completely exit the housing 9 on an unintentional triggering.

To move the internal piston back into its open position, the electric motor 35 is switched on. The spindle 19 is driven via the toothed wheels 31, 29 and 25. The external piston 7 moves axially to the right out of the housing 9 by the spindle rotation. The internal piston 5 is in the meantime still supported against the hose 1 or the rear wall 3 of the passage. As soon as the external piston 7 and the internal piston 5 are again completely pushed onto one another, the radial openings 14 in the internal piston 5 are again in the region of the cut-out 15 inside the external piston 7. The tip of the blocking bar 11 can again push between the balls 13 which are in turn moved radially outwardly through the openings 14 in the internal piston 5. The blocking bar 1 1 is pushed into the axial cut-out 6 of the internal piston 5 by the action of the spring 48 which acts on the rocker 41 for this purpose. The balls 13 again engage into the cut-out 15 in the external piston 7 as is shown in FIG. 4 and latch the external piston 7 and the internal piston 5.

If the electric motor 35 is now operated in the reverse direction, the spindle 19 pulls the external piston 7 to the left in the representation of the Figures. The internal piston 5 is also moved back due to the latching of the internal piston 5 in the external piston 7 and the fast closing clamp again moves to its open position.

The spring 17 again already starts to tension while the external piston 7 is again pushed over the internal piston 5 and stores energy for a new triggering process. It is possible in this way for a further pinching off process to be triggered as required on the returning of the internal piston 5 together with the external piston if e.g. a bubble is again already detected in the extracorporeal circuit during the return of the internal piston 5.

The fast closing clamp in accordance with the invention is in particular suitable for portable systems due to its compact and integral design.

REFERENCE NUMERAL LIST 1 hose
3 passage wall
5 clamp jaw, internal piston
6 axial cut-out at the rear end of the internal piston
7 holding apparatus, external piston
9 housing
11 blocking bar
12 hinge point
13 balls
14 radial openings
15 cut-out in the external piston
16 seat in the external piston
17 spring
18 seat at the internal piston
19 spindle
20 chamfer in the cut-out of the external piston
21 thread
23 bearing
25, 29, 31 toothed wheels
27, 33 grub screws
35 electric motor 37 holding plate
38 elongate hole
39 abutment bar
41 rocker
43 rocker center of rotation
45 electromagnet
47 actuation bar
48 spring
49 hinge point

The invention claimed is:

1. A fast closing clamp for the pinching off of hoses comprising the following:
   a) a clamp jaw with a clamping position, in which it can pinch off a hose, and an open position;
   b) a holding apparatus;
   c) a spring device which biases the clamp jaw with respect to the holding apparatus such that the clamp jaw is brought into the clamping position on the relaxation of the spring device;
   d) a latch device with which the clamp jaw and the holding apparatus can be latched to one another against the spring force of the spring device in a latched position; and
   e) a return mechanism for the movement of the holding apparatus relative to the clamp jaw until the holding apparatus and the clamp jaw are in their latched position relative to one another while the clamp jaw is in the clamping position, and for the movement of the holding apparatus together with the clamp jaw into the open position of the clamp jaw after the clamp jaw and the holding apparatus with the latching device have been latched to one another.

2. A fast closing clamp in accordance with claim 1, wherein the holding apparatus comprises a hollow part in which the clamp jaw is guided.

3. A fast closing clamp in accordance with claim 2, wherein the spring device comprises a spring supported, at the one end, against a seat inside the hollow part and, at the other end, against a seat in the clamp jaw.

4. A fast closing clamp in accordance with claim 1, wherein the latch device is mechanical.

5. A fast closing clamp in accordance with claim 4, wherein the latch device comprises at least one element which engages laterally from the clamp jaw into a cut-out of the holding apparatus in the latched state and frees the cut-out in an unlatched state.

6. A fast closing clamp in accordance with claim 5, wherein the at least one element is a ball which projects through a radial opening into the cut-out of the holding apparatus in the latched state, with the opening partly encompassing the ball and the ball not projecting out of the opening in the unlatched state.

7. A fast closing clamp in accordance with claim 1, wherein the latch device comprises a blocking bar which actuates the latch device and an electrical drive for the movement of the blocking bar, preferably an electromagnet.

8. A fast closing clamp in accordance with claim 7, wherein the electric drive is designed and arranged such that a current flow to the drive results in a movement of the blocking bar which results in an unlatching of the latch device.

9. A fast closing clamp in accordance with claim 1, wherein the return mechanism comprises a spindle drive.

10. A fast closing clamp in accordance with claim 1, comprising an abutment device which is made such that it bounds the movement of the clamp jaw triggered by the spring device.

11. A clamp for the pinching off of hoses, the clamp comprising:
    a clamp jaw being movable in a longitudinal direction between an open position and a clamping position;
    a holding apparatus being movable in the longitudinal direction relative to the clamp jaw;
    a latch device configured to latch the clamp jaw to the holding apparatus when the clamp jaw and the holding apparatus are in a latching position relative to each other so as to prevent the clamp jaw from moving with respect to the holding apparatus in the longitudinal direction, thereby preventing the clamp jaw from moving from the open position to the clamping position when the clamp jaw and the holding apparatus are latched together;
    a separating device that exerts a separating force between the clamp jaw and the holding apparatus such that the clamp jaw moves to the clamping position when the clamp jaw and the holding apparatus are not latched together; and
    a return mechanism configured to move the holding apparatus relative to the clamp jaw in the longitudinal direction when the clamp jaw and the holding apparatus are not latched together until the holding apparatus and clamp jaw are in the latching position relative to each other, the return mechanism also being configured to move the clamp jaw from the clamping position to the open position when the holding apparatus and clamp jaw are latched together.

12. A clamp in accordance with claim 11, wherein the separating device comprises a spring supported, at one end, against a seat inside the holding apparatus and, at the other end, against a seat in the clamp jaw.

13. A clamp in accordance with claim 11, wherein the latch device comprises at least one element which engages laterally from the clamp jaw into a cut-out of the holding apparatus when the clamp jaw and the holding apparatus are latched together.

14. A clamp in accordance with claim 13, wherein the at least one element is a ball which projects through a radial opening into the cut-out of the holding apparatus when the clamp jaw and the holding apparatus are latched together, such that the opening partly encompasses the ball.

15. A clamp in accordance with claim 11, wherein the latch device comprises:
    a blocking bar that actuates the latch device; and
    an electrical drive that moves the blocking bar.

16. A method of clamping a hose, the method comprising:
    positioning a clamp jaw in an open position that allows a flow of fluid through a hose, the clamp jaw being latched to a holding apparatus by a latch device, the relative longitudinal position between the clamp jaw and the holding apparatus when latched together being a latching position;
    manipulating the latch device to unlatch the clamp jaw from the holding apparatus, the clamp jaw moving in the longitudinal direction after being unlatched from the holding apparatus to a clamping position by a separating force tending to move the clamp jaw away from the holding apparatus, the clamp jaw preventing the flow of fluid through the hose while in the clamping position;
    moving the holding apparatus relative to the clamp jaw in the longitudinal direction until the holding apparatus and clamp jaw are in the latching position relative to each other while the clamp jaw is in the clamping position;

latching the clamp jaw to the holding apparatus using the latch device while the clamp jaw is in the clamping position; and moving the holding apparatus and clamp jaw while latched together until the clamp jaw is in the open position.

17. A method of clamping a hose in accordance with claim 16, wherein the separating force is a spring device.

18. A method of clamping a hose in accordance with claim 16, wherein:

manipulating the latch device to unlatch the clamp jaw from the holding apparatus comprises laterally removing at least one element from a cut-out formed in the holding apparatus; and latching the clamp jaw to the holding apparatus comprises moving the at least one element into the cut-out formed in the holding apparatus.

19. A method of clamping a hose in accordance with claim 18, wherein the at least one element is moved into the cut-out by a biasing force caused by a blocking bar and the at least one element is removed from the cut-out by removal of the biasing force.

* * * * *